United States Patent [19]

Godard et al.

[11] Patent Number: 4,647,162
[45] Date of Patent: Mar. 3, 1987

[54] APPARATUS FOR ILLUMINATING LIQUID IN A CONTAINER FOR CONTROL PURPOSES

[75] Inventors: Jean-Henri Godard, Bordeaux; Pierre Ometz, Saint-Aubin-de-Medoc; Jacques Labrador, L'Union, all of France

[73] Assignees: Societe Nationale Industrielle et Aerospatiale; Sanofi, both of Paris, France

[21] Appl. No.: 679,347

[22] Filed: Dec. 7, 1984

[30] Foreign Application Priority Data

Dec. 7, 1983 [FR] France ................ 83 19561

[51] Int. Cl.[4] .................. G02B 7/00; G01N 21/16
[52] U.S. Cl. ........................ 350/574; 356/240
[58] Field of Search .............. 356/427, 418, 240; 350/448, 449, 574

[56] References Cited

U.S. PATENT DOCUMENTS

| | | |
|---|---|---|
| 2,436,262 | 2/1948 | Miller . |
| 2,635,194 | 4/1953 | Kellogg et al. ............ 356/427 |
| 4,209,802 | 6/1980 | Fogg et al. ............... 356/240 |
| 4,428,673 | 1/1984 | Yoshida .................. 356/240 |
| 4,492,475 | 1/1985 | Takahashi ................ 356/427 |

FOREIGN PATENT DOCUMENTS 0086143 of 0000 European Pat. Off. .
682869 10/1939 Fed. Rep. of Germany .

Primary Examiner—John K. Corbin
Assistant Examiner—Vincent J. Lemmo
Attorney, Agent, or Firm—Armstrong, Nikaido, Marmelstein & Kubovcik

[57] ABSTRACT

An illumination device for a liquid contained in a container for checking the liquid. The device includes a device for positioning the container and a light source arranged to illuminate the liquid via the base of the container with a light beam aligned along the axis of the container. The invention resides in a mechanism for shaping the light beam issuing from the light source, disposed between the source and the base of the container, and which cooperates with the optical system constituted by the base itself and the liquid, if in contact with the base, in such a fashion that the beam passes substantially through the whole of the volume of the liquid without impinging on the side walls of the container which are in contact with the liquid. The image of the light source the other side of the mechanism for shaping and the container base is preferably located in the neighborhood of the end surface of the liquid, or past it. The device is of particular value in apparatus for checking pharmaceutical and food liquids in ampoules and bottles.

7 Claims, 6 Drawing Figures

APPARATUS FOR ILLUMINATING LIQUID IN A CONTAINER FOR CONTROL PURPOSES

BACKGROUND OF THE INVENTION

The invention relates to an illumination apparatus for a transparent liquid contained in a container transparent to the irradiation used and of which the lateral walls are parallel to the longitudinal axis for the purposes of control. It is particularly concerned with checking food liquids, injectable solutions and pharmaceutical preparations which are provided in particular in the form of bottles or ampoules of injectable product.

The check consists in detecting the presence of any solid particles in suspension, either natural or generated in the liquid product.

It is carried out generally by illuminating the liquid starting from a source of light placed laterally or at the base of the container. The observation can take place along the axis from the source, the occultation of a fraction of the light by the particles giving rise to their detection. Alternatively it can be carried out by observing along an axis different from that from the source to see reflections, refractions or diffractions stimulated by any particles present.

In the case of illumination through the base, known apparatus generally uses a light source and means allowing the light to penetrate through the base of the container. However these known apparatus have several disadvantages connected with the fact that they do not take account of the deformation of the light beam by the container itself. In effect the walls of the container behave as air liquid lenses which modify the beam of light; for example they make it converge or diverge, in particular as a function of the curvature of the walls. A luminous beam of light results which is deformed by the wall of the container, which does not illuminate the liquid to be checked in homogeneous fashion, that is to say the illumination produced in the body of the liquid varies from one point to another. In addition, these known apparatus illuminate without any distinction the container and the liquid. As a result of this, faults or writing which may be present on the walls of the container and which may thus be illuminated are a source of detection errors, these faults interfering with the luminous beam in the same way as the particles in suspension in the liquid and thus being confusable with them. The elimination of these erroneous detections can be obtained by lowering the level of illumination produced by the source, but this, as a result, diminishes in substantial fashion the luminous signals emitted by the particles and serving for their detection.

GENERAL DESCRIPTION OF THE INVENTION

According to the invention all these disadvantages are avoided thanks to an illumination apparatus for a transparent liquid contained in a container transparent to the radiation used and of which the lateral walls are parallel to a longitudinal axis, with the object of checking this liquid, comprising means for positioning the container and a light source for illuminating the liquid starting from the base of the container and along the axis of the container. In accordance with the invention this apparatus comprises means for shaping the luminous beam issuing from the source and which are disposed on the path of the beam between it and the base of the container and cooperating with the optical system constituted by the base itself in such a fashion that the beam takes a shape which traverses substantially the whole of the volume of the liquid without impinging on the side wall areas of the container in contact with the liquid, and in such a fashion that the image of the source opposite the shaping means and the base is situated in the neighbourhood of the end surface of the liquid or past it.

Thus in accordance with the invention account is taken of the dimensional characteristics and shape of the container as well as the nature of the liquid and its position in the interior of the container in order to produce, starting from the illumination device, a luminous beam such that on traversing the base of the container it is modified in such a way as to ensure optimum illumination of the liquid.

Preferably the light source is a secondary source the dimensions of which are compatible with those of the container and which is is shaped from a primary source through a first optical system, the means for putting into shape the beam issuing from the secondary source being constituted by a second optical system forming, in cooperation with the base itself, the image of the secondary source situated in the neighbourhood of the terminal surface of the liquid or past it.

The use of a primary luminous source and a secondary source, as stated here-above, permits the advantageous dissociation of the problems connected with the quantity of light to be produced and the problems connected with the formation of an image of the secondary source after it has passed through the second optical system and the container: the primary source or hot source is determined and dimensioned as a function of the necessary luminous energy for adequate illumination of the mass of liquid contained in the container while the secondary source or cold source is determined in a more precise fashion as a function of the dimensions and of the shape of the section of the container. Consideration of the apparatus shows that in order to obtain satisfactory adaptation the secondary source ought to have comparable dimensions with that of the container that is to say they should be less than this, by a ratio of 1 to 5. Furthermore, in order that the adaptation of the shape of the beam to that of the recipient is optimal, the apparent surface of the secondary source, in the axis of the illumination apparatus, ought to be similar in shape to the right cross section of the container. This can be effected either by choosing the same shape for the secondary source or by using a diaphragm having the shape required and which can be placed at the level of the source or at any point where an image of this forms.

The first optical system can consist of any means allowing the concentration of the light issuing from the primary source onto the secondary source. It can be formed by a single mirror, or by one or several lenses or again by association of both these means.

The second optical unit can also itself be formed by one or several lenses or by one or several mirrors of appropriate curvature.

A further embodiment of the invention relates to use with ampoules of low content such as pharmaceutical ampoules of a few millilitres capacity. The first optical system comprises advantageously in this case a fibre optic unit of cross-section of similar shape to that of the container, the inlet end of which receives the beam issuing from the primary source and the outlet end of which constitutes the secondary source and there is a diaphragm provided of section substantially equal to the interior cross-section of the container which is disposed between the second optical system and the base of the container.

The diaphragm can be constituted by means adapted to position the container. Preferably ampoules are located vertically, base downward, the end surface noted above being then constituted by the free surface of the liquid.

A second embodiment of the invention relates to bottles of large capacity, the diameter of which may be between several centimetres and a dozen centimetres such as bottles of large quantities of solutions or food liquids. The principle of the invention is then applied in different fashion since it is necessary to adapt the shape and the dimensions of the primary and secondary source ot the shape and dimensions of this type of container. It is necessary on the other hand to maintain the level of illumination, thus to augment the flux emitted by the primary source and as a result to augment the surface of this.

In certain cases one can maintain the apparatus noted relative to small ampoules and increase the diameter of the fibre optic. In the case where such a possibility is neither envisaged nor appropriate, it is necessary to use another device.

In such a device the first optical system concentrates the bundle on to a first diaphragm of cross section matching that of the container which is located between the two optical systems and which constitutes the secondary source and there is provided a second diaphragm of cross section substantially equal to the interior cross section of the container which is located between the second optical system and the base of the container.

The first diaphragm can if desired be combined either by way of position or by way of diameter with the support of the final optical element of the first optical system. As for the second diaphragm, it may be formed by means for positioning the container.

Preferably the container or bottle is disposed vertically, base upward, the end surface noted being then constituted by the bearing surface for the liquid on another wall of the end of the container.

The means for putting the beam into shape can comprise a flat returning mirror which is located across the beam between the first optical group and the base of the recipient. Such a mirror permits the luminous beam coming from the primary source to be turned for example in a direction offset by 90° relative to its incidence direction in such a fashion as in particular to limit the vertical extent of the container checking assembly.

The end surface of the liquid noted is that through which the luminous beam emerges from the liquid after having passed through it. In the case of little ampoules disposed with their base downward, the beam penetrates into the liquid through its contact surface with the base of the ampoule and leaves it through its free surface, which thus constitutes the terminal surface of the liquid. In the case of large bottles disposed bottom up, the luminous beam penetrates into the liquid through its free surface which is facing the base of the bottle, and it emerges therefrom via its surface in contact with the neck of the bottle which thus constitutes the terminal surface of the liquid.

DESCRIPTION OF PREFERRED EMBODIMENTS

The desciption which follows is to illustrate two embodiments of the invention set out above, by way of non-limitative examples. FIGS. 1 to 4 attached relate to an illumination device for small ampoules while FIG. 5 relates to an illumination device for large bottles. More precisely:

FIG. 6 illustrates a specific realization of an illumination device for small ampoules.

Figure 1:
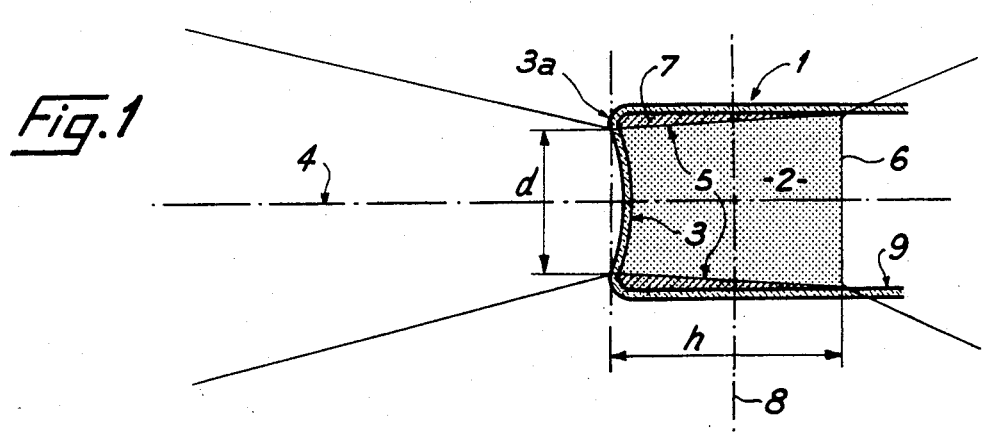
FIG. 1 shows the theoretical path of the luminous beam arranged relative to a cylindrical ampoule with a concave base.

In what follows it will be shown how the principle of the invention has been applied to the illumination of ampoules of generally cylindrical form and having a concave bottom which contain a pharmaceutical liquid to be checked, the illumination taking place starting from the base. FIG. 1 shows in particular such an ampoule 1 containing a liquid 2. This ampoule does not have to be cylindrical. The important thing is that is side walls are parallel to a longitudinal axis 4. To assist illustration, this ampoule 1, resting essentially vertically on a support, base down, is shown here horizontally.

Initially one starts by establishing the geometrical form of the base 3 of the ampoule, in such a fashion that it is present on several specimens of ampoules 2 and 5 millilitres content. It has been found that the base of the ampoule has a radius of curvature varying in accordance with the distance from the point of measuring this radius to the axis 4 of the ampoule, between several millimetres and infinity. This ampoule base merges with the cylindrical part of the ampoule via a small convex radius 3a. This radius 3a does not allow light to be transmitted correctly to the liquid 2 from the exterior of the ampoule 1 and accordingly it should not be used to illuminate the liquid.

Calculations show that the diameter "d" of the base of the remaining part of the ampoule which has the concave form, or the "useful diameter" corresponds approximately to a fixed proportion of the exterior diameter of the ampoule, whatever the ampoule.

It has also been additionally determined by measurements and calculations that the average radius of curvature of the base of the ampoule in such a fashion as to assimilate this into a simple optical system, should be one dioptre air/liquid divergent with a single curvature. It has been noted that from one ampoule to another this average radius of curvature varies. The description above shows how the apparatus according to the invention permits these variations of radius of curvature to be, in large part, taken out of account.

After having studied the optical system constituted by the base of the ampoule, it will not be explained how one can incorporate it. The ideal luminous beam of rays for illuminating the liquid 2 would have, during it path between the base 3 of the ampoule 1 and the meniscus 6 formed by the free surface of the liquid, a cylindrical envelope perfectly matching the interior side wall 9 of ampoule 1 in such a fashion as to illuminate the whole of the liquid 2. However, and as explained above, the base of the ampoule has a peripheral circular radius of curvature 3a which cannot be used. As a result, a theoretical beam of rays will now be defined which takes account of this limitation.

On FIG. 1 the envelope 5 of the theoretical luminous beam has been traced which permits, in accordance with the invention, the liquid 2 to be illuminated in optimum fashion. This beam emerges from a light source which is not shown and which is situated to the left of the ampoule 1 in such a fashion that the beam of rays penetrates into the amouple 1 starting from its base 3 and along the direction of its longitudinal axis 4. This beam of rays converges towards the base 3 in such a fashion as to pass through this in accordance with the useful diameter "d" relative to the concave zone of the base. On the other side the beam diverges slightly to intersect in a straight line the circle formed by the meniscus 6 of the free surface of the liquid 2 bearing against the interior wall 9 of the ampoule 1. This free surface constitutes the end surface of the liquid stated through which the beam emerges. In this fashion almost the whole of the volume of the liquid is traversed by the beam of rays with the exception of the hatched circular area 7 and this without the beam meeting any portion of the lateral walls of the ampoule in contact with the liquid. Above the meniscus 6 the beam can diverge indifferently and impinge on the upper zone on the wall of the ampoule as shown in FIG. 1. In fact the observation of the liquid illuminated starting from base 3 normally takes place along an axis 8 perpendicular to the axis of illumination 4 and it is known to mask all radiation emerging from the zone of the ampoule located above the liquid or emerging from the light source itself.

Advantageously the illumination device is conceived in such a fashion that the image of the light source through the apparatus and the base of ampoule 3 should be located in the plane of meniscus 6. In effect the image of the source corresponds to a convergence zone of the beam, above which it diverges. Also if this image forms before the meniscus 6, the beam would meet the ampoule wall zones in contact with the liquid, and would be the origin of detection errors. If on the other hand this image is formed above the meniscus 6, the luminous yield in the body of the liquid would be thereby diminished. However this second configuration can be conceived of.

Figure 2:
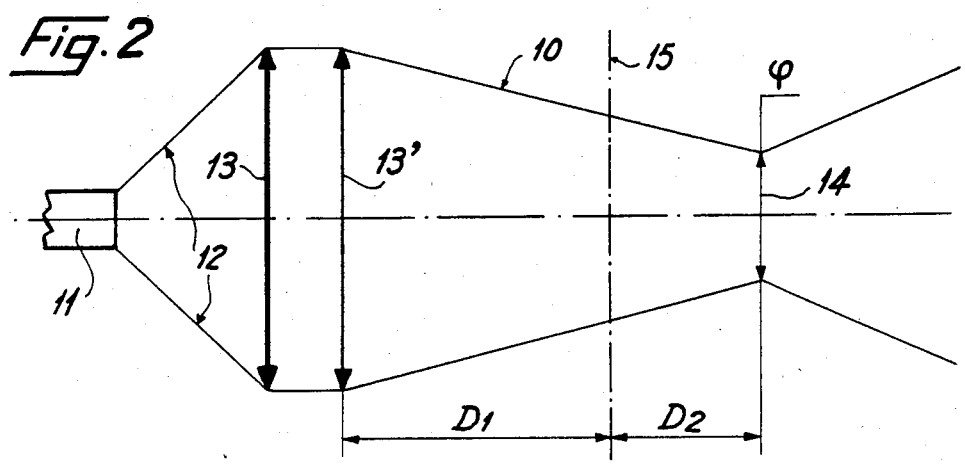
FIG. 2 shows the beam of light rays produced by the illumination device in accordance with the invention and which permit the illumination of an ampoule as defined by FIG. 1.

FIG. 2 shows the beam of light rays 10 issuing from the optical device in accordance with the invention which, when it is placed facing the base of the ampoule, should spread out according to the shape defined in FIG. 1. The base of the ampoule being one dioptre divergent, the beam 10 will be convergent towards the base of the ampoule in such a fashion that in association with it it produces (FIG. 1) the envelope 5 which is quasi-parallel to the side walls of the container. There has been drawn at 11 a light source which is not a point light source and which is circular. Its emergent light beam 12 diverges by a certain angle. A device or optical system for shaping the beam 12, of which only the theoretical entry and exit surfaces 13 and 13' have been drawn, capture the bundle 12 in such a fashion as to recover if possible all of the light issuing from source 11. The optical system is such that past the theoretical exit face 13' the light emerges in accordance with beam 10 which converges towards an image 14 of the source 11 and which spreads itself out divergently past this image. The beam of light rays 10 should, cooperating with the base of the ampoule, give rise to envelope 5 (FIG. 1) and should produce a new image at the level of the meniscus 6. Such a beam of light is defined by three parameters: The distance $D_1$ between the theoretical exit face 13' of the second optical system and the plane 15 on which ultimately the base of the ampoule rests, the distance $D_2$ between the plann 15 and the image 14 and finally the diameter $\phi$ of the image 14. Knowledge of these parameters will permit the real construction of the illumination device to be deduced.

The distance $D_1$ can be chosen identical for all types of ampoule which are to be checked in such a fashion that the diameter of the beam 10 where it intersects plane 15 corresponds to the greatest useful diameter "d" of the ampoule. Thus for such ampoules, it is not necessary to use a diaphragm to reduce the diameter of the beam 10 to the useful diameter "d".

The distance $D_2$ is chosen not by taking into account the radius of curvature of the base of the ampoule, but in considering that this base is flat and in such fashion the image 14 is located across such an ampoule in the plane of the meniscus of the liquid. In practice distance $D_2$ is a function of the height of filling "h" and the refractive index of the liquid.

Finally it is through the determination of the diameter $\phi$ of the image 14 that one takes into account the radius of curvature of the real ampoule. It has been chosen as large as possible as function of the possibilities of the illumination device in such a fashion as to illuminate the liquid best and this for an ampoule of radius of curvature the smallest, such as would emerge from measurements and calculations noted above starting from a selection of representative ampoules. Thus the beam of light rays in the interior of the ampoule is the most divergent which can be produced. The practical determination of the optimum value of $\phi$ is effected graphically for a given size of ampoule. It is deduced by geometrical similarity for other sizes of ampoules. It should be noted that so determined the value of $\phi$ permits the illumination of all the ampoules of the same size since these have by definition a base of average radius of curvature greater than the radius taken as reference. The beam which crosses the base thus diverges to a small extent and is thus accordingly always contained in the interior of the container, even if the illumination is a little less wide. The illumination device according to the invention thus does not require systematic regulation in order to adapt itself to the nevertheless variable characteristics of the ampoules.

Figure 3:
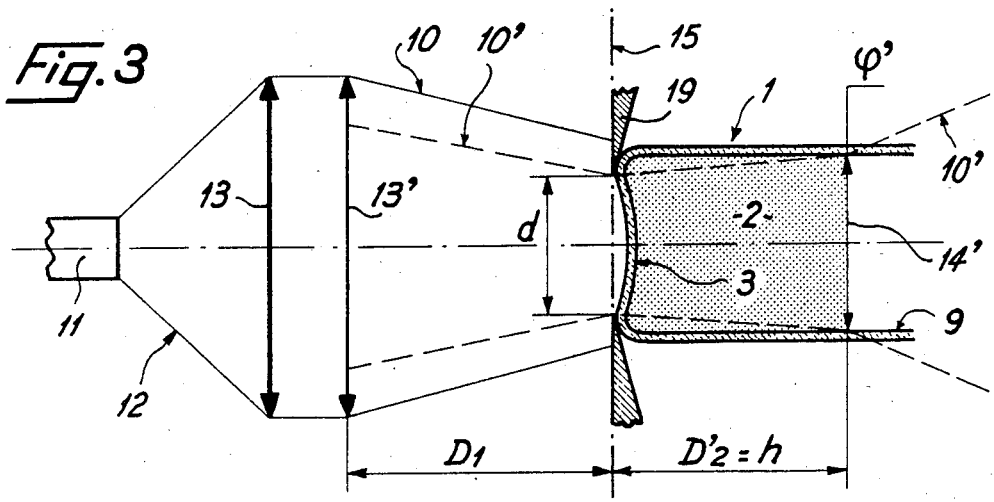
FIG. 3 shows the beam of rays obtained when the ampoule is located in front of the illumination device.

FIG. 3 and FIG. 6 share the ampoule 1 placed in front of the source 11 and the optical system indicated by the theoretical entry and exit faces 13 and 13'. The source 11, the optical system 13 and 13' and the ampoule 1 are disposed coaxially. There results from this (FIG. 2) without the ampoule, a beam 10 of characteristics ($D_1$, $D_2$, $\phi$) defined above. However it is necessary to adapt the diameter of the beam 10 to the useful diameter "d" of the ampoule in such a fashion as to avoid all useless and damaging illumination and to obtain the conical shape of the bundle shown in FIG. 1. Also there is placed a circular diaphragm 19 in the plane 15 at the bottom of the ampoule, the diameter of the opening of which is equal to "d" (FIG. 3).

Thus a portion of the beam 10' which passes through the liquid 2 and comes to intersect the interior lateral wall 9 at a distance $D'_2$ from the plane 15 which is equal to the height of filling "h". This beam 10' forms in this region an image 14' of the source 11 which has a diameter $\phi'$ equal to the interior diameter of the ampoule. Above this the beam 10' diverges generally.

The diaphragm 19, if it limits the entering beam 10, does not modify either the distance $D_2$ nor the diameter defined above and as a result does not disturb the path of the beam 10' which results from it.

An illumination device appropriate to produce a luminous beam as defined in FIG. 2 can comprise a fibre optical member of which one end is connected to a primary light source or heat source and of which the other end constitutes the cold course of the illumination device.

Preferably the source 11 is a secondary source shaped from a primary source which is not shown via a first optical condenser system which is likewise not shown. The optical system 13, 13' shown is then a second optical system forming the image 14' of the secondary source 11. The first optical system can in particular comprise a fibre optic element the entry of which is connected to the primary source or hot source and the exit of which constitutes the secondary source or cold source as shown in FIG. 6.

This arrangement advantageously permits distancing the hot source which dissipates heat from the ampoules to be checked the liquid in which does not therefore run the risk of heating up. Furthermore several fibre optic elements can start from the same heat source to illuminate different ampoules disposed on a common support and checked one by one or simultaneously. The entry to the fibre optic element is connected to the hot source by an optical system which condenses in fashion known per se the light issuing from the source towards this entry; this optical system comprises in particular a mirror and one or more lenses. At the outlet of the fibre optic element there is placed at least one lens permitting essentially the recovery of the beam emerging from the optical fibre and to make this beam converge towards the base of the ampoule. A diaphragm is located between this lens and the base of the ampoule.

Different control means for this illumination device are possible. The distance between the outlet of the fibre optic element and the lens disposed in front of this outlet and/or the distance between this lens at the base of the ampoule can be arranged adjustably. In addition the diameter of the diaphragm can also be adjustable.

Advantageously the single lens disposed in front of the outlet from the fibre optic element can be replaced by at least two lenses or groups of lenses which are not juxtaposed. This approach allows a supplementary control parameter to be introduced for this optical system, which is the distance between these lenses or groups of lenses.

Figure 4:
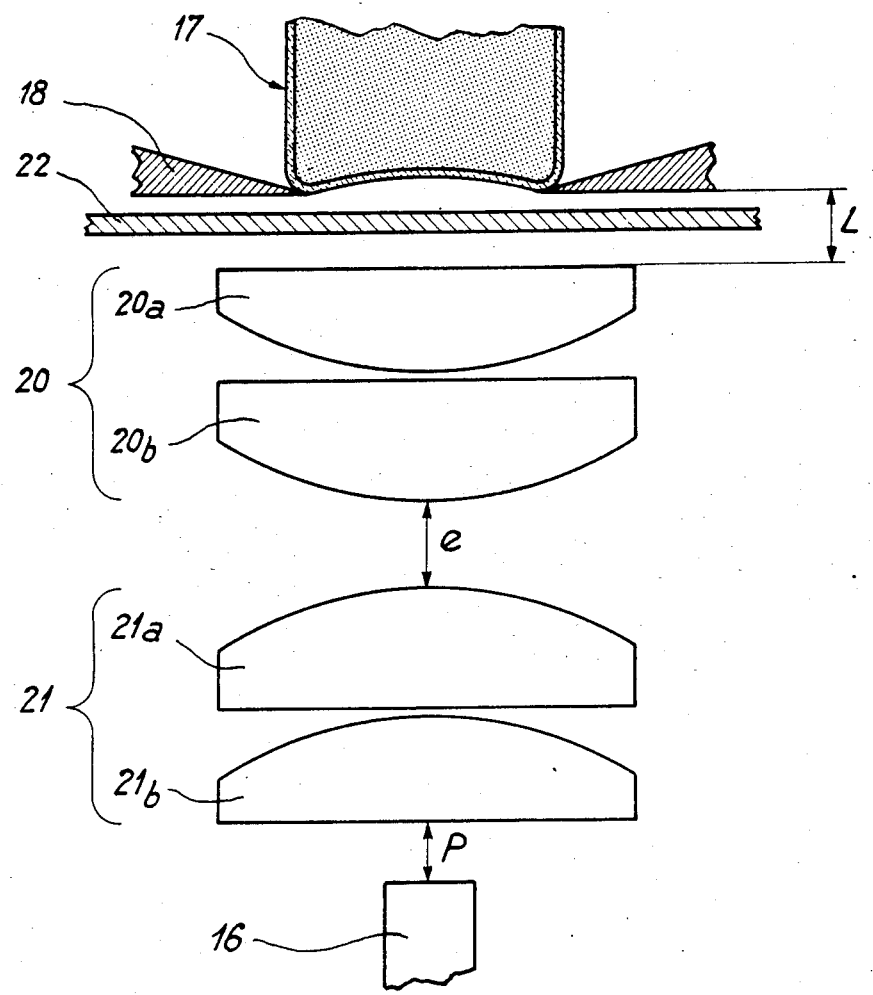
FIG. 4 shows a specific embodiment of the illumination apparatus of the preceding Figures.

An illumination device adapted to the dimensions of pharmaceutical ampoules of 2 to 5 milliliters capacity with a concave base is shown on FIG. 4. Its characteristics are bound up with an existing mechanism for checking ampoules on which it has to be fitted. If one were starting afresh, this device could be conceived differently. It comprises an outlet for a fibre optic member 16 disposed along the axis of the ampoule 17 positioned at a distance above the outlet 16, the entry to the fibre optic member being connected to a primary light source which is not shown such as a filament lamp. The ampoule 17 rests on a support 18 hollowed out circularly according to the useful diameter of the ampoule and advantageously playing the role of diaphragm. Between the outlet of fibre optic 16 and the support 18 there are successively disposed along the axis of the ampoule two lenses which are provided for reasons of conveniences in the form of two doublets 20, 21 of elemental planoconvex lenses 20a, 20b, 21a, 21b. The two lenses of each doublet are juxtaposed. Their convex faces are oriented in the same sense and opposite those of the other doublet.

A protective glass 22 is located between the lens 20a next to the base of the ampoule and this in such a fashion as to protect the optical system which is otherwise enclosed in a casing which is not shown, being traversable all the time by the luminous bundle. The spacing "e" between the two lens doublets as well as the spacing "p" between the lens 21b and the outlet of the fibre optic member 16 are adjustable by appropriate means. Their value, determined by numerical calculation taking into account the conditions noted above, can be determined after experimentation.

The illumination device in accordance with the invention efficaciously improves the maximum level of illumination at the interior of the ampoule, to level above which the defects or inscriptions on the wall generate erroneous detections: For example the outlet of the fibre optic member 16 placed alone in front of the base of ampoule does not permit an illumination level of greater than 90,000 lux to be exceeded in the body of the liquid on the axis and at one centimetre from the base of the ampoule. Using the device according to the invention this illumination rises to 450,000 lux, bringing a gain equal to 5. This means that the observed surface of each solid particle in the body of the liquid is 5 times better illuminated. The quantity of light received by the detector device for particles being proportional to the surface of these particles, one can also say that one is able to detect particles of surface 5 times less, that is to say of diameter more than twice as small, as with the fibre optic member alone.

The optical system described in the example noted above is not unique. It depends to a large extent on the type of container to be illuminated. Generally the illumination device in accordance with the invention can be formed by any optical system which allows the creation, starting from the source, of the image 14 of FIG. 2. This system can be effected with the aid of mirrors of lenses or of any combination of these two components. the choice of intervening components depends on the principle adopted but also on theoretical imperatives or techniques which are not directly connected such as for example the necessity of changing the shape of the source, the choice of a different range of wavelengths or the use of mirrors if the bottles are of substantial diameter.

A substantial improvement can be obtained by adapting the shape of the source to the shape of the container, as noted above.

The flexibility of the optical system can be advantageously improved in certain cases by placing a diaphragm limiting the extent of the bundle so that it is across the base of the container, as in the example described.

The fibre optic device described above relates initially to the illumination of small ampoules. As explained above, its adaptation to large bottles can be effected up to a certain point, particularly by increasing the diameter of the fibre optic element. Above this it is necessary to conceive of a further apparatus illustrated in FIG. 5.

On this Figure there is shown a cylindrical bottle 30 of large dimension (its content is for example equal to one litre). The bottle 30 drawn horizontally is in reality disposed vertically, its base 31 being in the upper portion. It is partly filled with a liquid 32 to be checked, this liquid resting on the neck 33 and the stopper and having a free surface 34 facing the base 31.

Various optical elements are arranged laterally of the base of bottle 30 and coaxially to the bottle 30, the axis of which is designated by reference numeral 46. A first optical system allows the light from a primary source 35, constituted for example by an iodine lamp filament, to be concentrated on a first diaphragm 36 defining defining said secondary source.

This system located between the source 35 and the first diaphragm 36 comprises a group of two lenses, that is aspheric lens 37 corresponding substantially to a hemisphere and a plano-convex lens 38. The diameter of these lenses is substantially greater than that of the first diaphragm 36. These lenses are disposed facing one another in such a way that their convexities are turned one to another. The first optical system comprises also a concave mirror 39 inthe form of a spherical cap the diameter of which has dimensions similar to those of the above described lenses. This mirror 39 is disposed coaxially relative to the group of lenses 37, 38 on the side of the source 35 opposite the aspheric lens 37, its concavity being opposed to this lens. The centre of curvature of the mirror 39 coincides with the source 35.

The means for putting a luminous beam into shape comprise, apart from the group of lenses 37, 38, the mirror 39 and the first diaphragm 36, a complementary lens 40 constituting the second optical system. The complementary lens 40 is plano-concave and its diameter is equal to the useful diameter of the bottle 30. Its convexity is directed towards the base 31 of bottle 30 and located at an appropriate distance from this base. A second diaphragm 41 can if desired limit the width of the beam to the level of the base of the container. This diaphragm can be combined with the support for the complementary lens 40 or one of the positioning means for the bottle 30. The separation between the complementary lens 40 and the plano-convex lens 38 of the group of lenses is of the order of magnitude of the sum of the focal distances of these two lenses.

Figure 5:
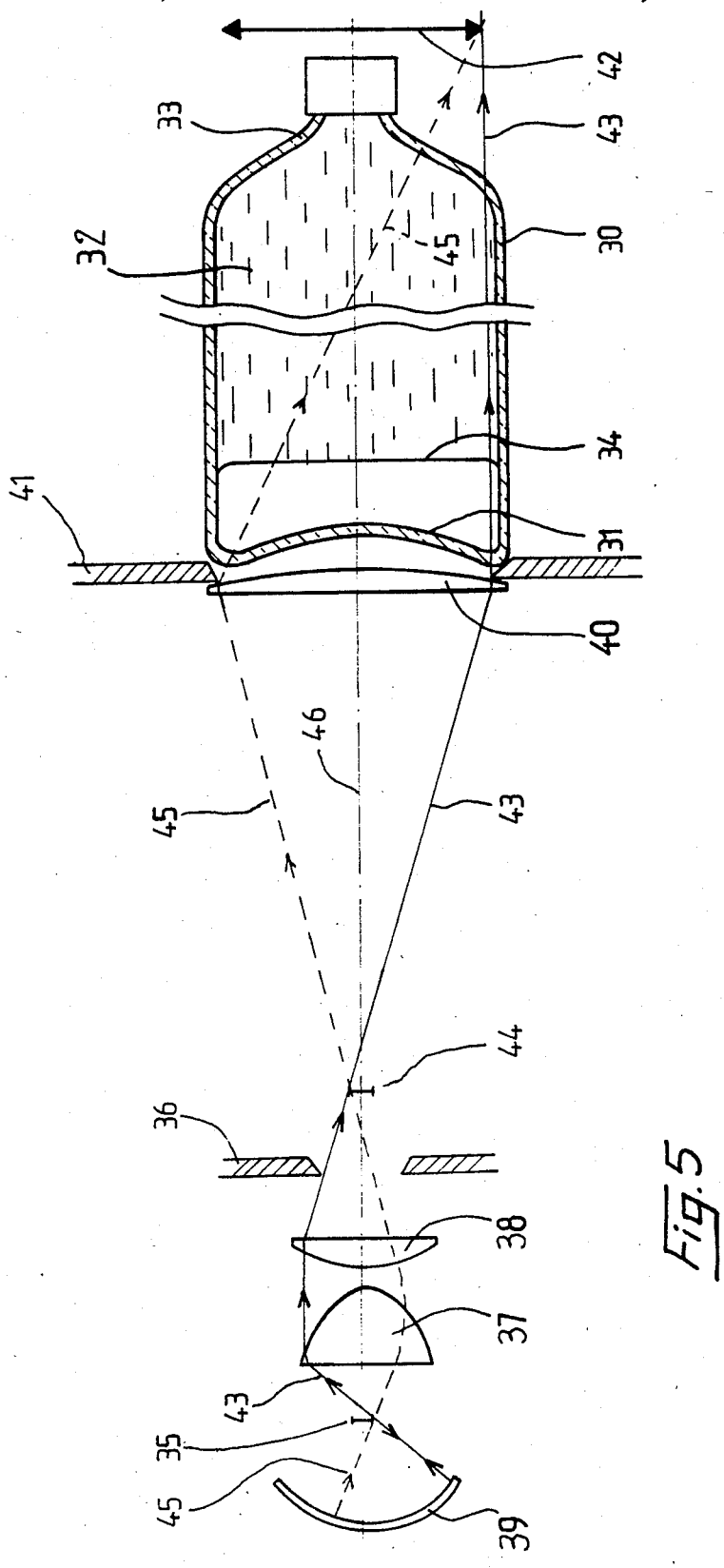
FIG. 5 illustrates a specific realisation of an illumination device for large bottles.

In operation, the complementary lesn 40 cooperating with the plane dioptre constituted by the free surface 34 of the liquid 32 contained in the bottle 30 gives from the first diaphragm 36 constituting the secondary source an image 42 located either at the level of the end face of the liquid or past it as shown on FIG. 5. The terminal surface of the liquid starting from which the luminous beam emerges from the liquid is constituted here by the surface through which the liquid 32 bears on the neck 33 of bottle 30; the free surface 34 of the liquid 32 is the entry surface for the beam into this liquid. In this example the image 42 has a diameter equal to the interior diameter of the bottle 30. The beam between the limits formed on the one hand by the second diaphragm 41 and on the other hand by the final image 42 of the first diaphragm 36 has a cylindrical envelope, the second diaphragm 41 and the final image having a diameter equal to the interior diameter of the bottle 30. FIG. 5 shows the path of a ray 43 coinciding with the cylindrical envelope.

This ray 43 issues from the source 35 limited by a cone of light emission from the source 35 captured by the asphehric lens 37, this emission cone being augmented by the cone to which it is opposed and which is reflected by the mirror 39. The strongly divergent beam 43 is straightened by the group of lenses 37, 38. It is then directed towards the edge of the opening of the first diaphragm 36, then towards a point of convergence 44 representing the theoretical point image of the filament source 35, the opening of the first diaphragm 36 defining an intermediary image of the primary source 35; the ray 43 meets then the peripherl zone of the complementary lens 40; it passes through this, passes near the edge of the opening of the second diaphragm 41 and then proceeds along a parallel path to the axis of the bottle 30, crosses the base 31 and goes along the internal face of the wall of the bottle 30 while being adjacent to this face. The optical path of the ray 43, as in addition to that of all the other rays passing through base 31, is not substantially changed by this base, which is not in contact with the liquid 32 and which behaves like a layer with parallel faces.

The ray 43 then meets the free surface 34 of the liquid or the entry surface into the liquid. This being very close to flat it does not change the trajectory of ray 43. In contrast in the case of a bottle of small diameter the free surface in the form of a meniscus risks the path of the rays in the liquid 32 being disturbed since it would constitute a divergent air/liquid dioptre. In this last case, the modification of the conversions and/or of the position of the complementary lens 40 would permit the presence of this dioptre to be taken into account, analogous to that formed by the base of pharmaceutical ampoules.

Finally the ray 43 continues its trajectory in a straight line in the body of liquid 32, then outside of bottle 30.

A second ray of light 45 permits the axial position and the diameter of the image 42 of the first diaphragm 36 to be determined. This ray 45 comes to impinge on the complementary lens 40 at a point opposite to the corresponding point for ray 43. It obliquely crosses the bottle 30 and defines above this bottle the envelope of the luminous beam which then diverges. The point of intersection between the two rays 43 and 45 above the bottle 30 defines the axial position and the diameter of the image 42.

Naturally the invention is also applicable to the illumination of containers of large dimensions disposed bottom down. In this case it is necessary to take into account the influence of the base of the container on the luminous beam, as explained in detail with respect to FIGS. 1 to 3. Thanks to an appropriate choice of the focal distance and of the position of the second optical system, one can obtain convergence of the beam between the second optical system and the base of the container in quasi-cylindrical beam of rays.

The invention finds its application particularly in thé detection of flaws in food and pharmaceutical liquids.

We claim:

1. In an illumination device for illuminating a transparent liquid contained in a container transparent to the illuminating radiation and having lateral side walls parallel to a longitudinal axis and a base, for the purpose of checking the condition of the liquid, and including a light source, means to produce a light beam, and means for positioning the container relative to the light source and light beam to illuminate the liquid with the light beam passing through said base of said container and along said axis, the improvement comprising the provision of means for shaping the light beam which issues from said light source located along the path of the beam between said light source and said base of said container and cooperating with an optical system constituted by said base itself in such a fashion that said shaped beam passes through substantially the whole of the volume of the liquid in said container without meeting the side walls of said container which are in contact with the liquid, and in such a fashion that an image of said light source remote from said shaping means and said container base is located inthe neighbourhood of an end surface of the liquid remote from said source or beyond it.

2. The illumination device of claim 1 wherein the light source is a secondary source the dimension of which are compatible with those of the container, said secondary source being formed from a primary source by a first optical system, said means for shaping the light beam issuing from the secondary source being constituted by a second optical system forming, in cooperating with said base itself, an image of the secondary source located in the neighbourhood of the end surface of the liquid or beyond it.

3. The illumination device of claim 1 and including at least one optical system comprising at least one lens and/or mirror.

4. The illumination device fo claim 2 adapted to illuminate an ampoule of low capacity, wherein said first optical system comprises a fibre optic member of cross-sectional shape matching that of the ampoule, an inlet-end of said fibre optic member receiving the light beam issuing from said primary source and an outlet end of said fibre optic member constituting said secondary source and including a diaphragm of cross-section substantially equal to an interior cross-section of the ampoule, said diaphragm being disposed between said second optical system and the base of the ampoule.

5. The illumination device of claim 2 adapted to illuminate a bottle of substantial capacity, wherein said secondary source includes a first diaphragm of cross-section similar in shape to that of the bottle and disposed between said first and second optical system, said first optical system being arranged to concentrate said light beam onto said first diaphragm, and a second diaphragm of cross-section substantially equal to an interior cross-section of the bottle and disposed between said second optical system and the base of the bottle.

6. The illumination device of claim 4 wherein said means for positioning includes means for holding the ampoule with its axis disposed vertically, with the base of the ampoule downwards, whereby said end surface of the liquid is constituted by the upper free surface of the liquid.

7. The illumination device of claim 6 wherein said means for positioning the container includes means for positioning said bottle with its axis disposed verticdally, base upwards, whereby said end surface of the liquid is constituted by a bearing surface of the liquid on an end wall of said bottle.

* * * * *

UNITED STATES PATENT AND TRADEMARK OFFICE
CERTIFICATE OF CORRECTION

PATENT NO. : 4,647,162

DATED : March 3, 1987

INVENTOR(S) : JEAN-HENRI GODARD ET AL

It is certified that error appears in the above-identified patent and that said Letters Patent is hereby corrected as shown below:

On the cover page, Item [73], change "Societe Nationale Industrielle et Aerospatiale" to --- Aerospatiale Societe Nationale Industrielle ---.

Signed and Sealed this

Eighteenth Day of August, 1987

*Attest:*

DONALD J. QUIGG

*Attesting Officer*      *Commissioner of Patents and Trademarks*